(12) United States Patent
Schollenberger et al.

(10) Patent No.: US 9,383,242 B2
(45) Date of Patent: Jul. 5, 2016

(54) FLUID CHARACTERISTIC DETERMINATION OF A MULTI-COMPONENT FLUID WITH COMPRESSIBLE AND INCOMPRESSIBLE COMPONENTS

(75) Inventors: Frederick Scott Schollenberger, Boulder, CO (US); Joel Weinstein, Boulder, CO (US); David John Shepherd, Auckland (NZ)

(73) Assignee: Micro Motion, Inc., Boulder, CO (US)

( * ) Notice: Subject to any disclaimer, the term of this patent is extended or adjusted under 35 U.S.C. 154(b) by 0 days.

(21) Appl. No.: 14/413,990

(22) PCT Filed: Aug. 1, 2012

(86) PCT No.: PCT/US2012/049133
§ 371 (c)(1),
(2), (4) Date: Jan. 9, 2015

(87) PCT Pub. No.: WO2014/021884
PCT Pub. Date: Feb. 6, 2014

(65) Prior Publication Data
US 2015/0160056 A1    Jun. 11, 2015

(51) Int. Cl.
*G01F 1/74* (2006.01)
*G01F 1/84* (2006.01)
*G01N 9/26* (2006.01)
*G01N 9/32* (2006.01)

(52) U.S. Cl.
CPC *G01F 1/849* (2013.01); *G01F 1/74* (2013.01); *G01F 1/8436* (2013.01); *G01N 9/26* (2013.01); *G01N 9/32* (2013.01)

(58) Field of Classification Search
CPC .............. G01F 1/74; G01F 1/60; G01F 1/84
USPC ........... 73/861.04, 861.17, 861.356, 861.357
See application file for complete search history.

(56) References Cited

U.S. PATENT DOCUMENTS

| | | | |
|---|---|---|---|
| 5,099,697 A | 3/1992 | Agar | |
| 6,338,276 B1 * | 1/2002 | Durando | G01F 1/34 73/200 |
| 6,345,536 B1 | 2/2002 | Morrison et al. | |
| 6,847,898 B1 | 1/2005 | Chen et al. | |
| 7,188,534 B2 * | 3/2007 | Tombs | G01F 1/74 73/861.356 |
| 2002/0034166 A1 | 3/2002 | Barany et al. | |
| 2004/0182172 A1 | 9/2004 | Richards | |
| 2005/0061060 A1 * | 3/2005 | Gysling | G01F 1/74 73/32 A |
| 2007/0180929 A1 * | 8/2007 | Rieder | G01F 1/74 73/861.17 |

* cited by examiner

*Primary Examiner* — Jewel V Thompson
(74) *Attorney, Agent, or Firm* — The Ollila Law Group LLC

(57) ABSTRACT

A method for determining fluid characteristics of a multicomponent fluid is provided. The method includes a step of measuring a first density, $\rho_1$, of a multicomponent fluid comprising one or more incompressible components and one or more compressible components at a first density state. The method further includes a step of adjusting the multicomponent fluid from the first density state to a second density state. A second density, $\rho_2$, of the multicomponent fluid is then measured at the second density state and one or more fluid characteristics of at least one of the compressible components or the incompressible components are determined.

15 Claims, 3 Drawing Sheets

FLUID CHARACTERISTIC DETERMINATION OF A MULTI-COMPONENT FLUID WITH COMPRESSIBLE AND INCOMPRESSIBLE COMPONENTS

TECHNICAL FIELD

The embodiments described below relate to, multi-component fluids, and more particularly, to a method for determining various fluid characteristics of a multi-component fluid with one or more compressible components and one or more incompressible components.

BACKGROUND OF THE INVENTION

Vibrating fluid sensors, such as Coriolis mass flow meters and vibrating densitometers typically operate by detecting motion of a vibrating conduit that contains a flowing material. Properties associated with the fluid in the conduit, such as mass flow, density and the like, can be determined by processing measurement signals received from motion transducers associated with the conduit. The vibration modes of the vibrating material-filled system generally are affected by the combined mass, stiffness and damping characteristics of the containing conduit and the material contained therein.

A typical vibrating fluid meter includes one or more conduits that are connected inline in a pipeline or other transport system and convey material, e.g., fluids, slurries and the like, in the system. Each conduit may be viewed as having a set of natural vibration modes, including for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation by cabling, such as by two independent pairs of wires. The instrumentation receives signals from the two pickoff sensors and processes the signals in order to derive a mass flow rate measurement.

Vibrating fluid meters offer high accuracy for single component flows. However, when a vibrating fluid meter is used to measure fluids including entrained gas, gas including entrained liquid droplets, or other types of fluids including both compressible and incompressible components, the accuracy of the meter can be significantly degraded. Entrained gas is commonly present as bubbles in the flow material. One problem caused by gas bubbles is decoupling. Small bubbles typically move with the liquid flow material as the flow meter is vibrated. However, larger bubbles do not move with the liquid during vibration of the flow tube. Instead, the bubbles can be decoupled from the liquid and can move independently of the liquid. Consequently, the liquid can flow around the bubbles. This adversely affects the vibrational response of the fluid meter.

The size of the entrained gas bubbles can vary, depending on the fluid velocity, viscosity, surface tension, and other parameters. The extent of the decrease in performance is not only related to how much total gas is present, but also to the size of the individual gas bubbles in the flow. The size of the bubbles affects the accuracy of the measurement. Larger bubbles occupy more volume and decouple to a greater extent, leading to greater error in measurements of the flow material. Due to the compressibility of a gas, the bubbles can change in gas amount yet may not necessarily change in size. Conversely, if the pressure changes, the bubble size can correspondingly change, expanding as the pressure drops or shrinking as the pressure increases. This can also cause variations in the natural or resonant frequency of the flow meter.

Vibrating fluid meters are used to perform mass flow rate and density measurements for a wide variety of fluid flows. One area in which Coriolis flow meters can be used is in the metering of oil and gas wells. The product of such wells can comprise a multicomponent fluid, including the oil or gas, but also including other components, such as water and air, for example. It is highly desirable that the resulting metering be as accurate as possible, even for such multicomponent flows. Further, in such situations, a user often wants to know not only the overall flow rate and density of the fluid, but other fluid characteristics, such as the density of the liquid phase and the flow rate of the individual components of the multi-component flow. Often, the Coriolis flow meter will measure only an overall flow rate and density of the fluid. In the case of two liquid components of known density, it is possible in prior art flow meters to determine the individual component fractions and flow rates. The flow meter electronics currently on the market make the assumption that the fluid flow only contains oil and water and use equations (1) and (2) to determine the amount of each component. This algorithm is known in the oil and gas industry as a Net Oil Computer.

$$\phi_o + \phi_w = 1 \tag{1}$$

$$\rho_{measured} = \phi_o \rho_o + \phi_w \rho_w \tag{2}$$

Where:
$\phi_o$ is the volume fraction of oil;
$\phi_w$ is the volume fraction of water;
$\rho_{measured}$ is the fluid density measured by the vibrating fluid meter;
$\rho_o$ is the oil density; and
$\rho_w$ is the water density.

Using equations (1) and (2), if the water and oil densities are either known or assumed, then the volume fractions for the oil and water can be determined. With the volume fractions determined, the flow rate of the individual components can be determined. It is important to note that the measured density in equation (2) is actually slightly inaccurate due to decoupling between the two different components. However, because the density of water and oil are similar, the decoupling is very small and measurements are generally accurate enough.

However, when a system only uses equations (1) and (2), and if entrained gas is present, the resulting lower overall fluid density is incorrectly interpreted to be caused by higher oil volume fraction and thus, the meter electronics outputs a higher oil flow rate and overall amount of oil in the stream. In many real-world applications, the fluid may contain some gas, which may drastically reduce the measurement accuracy of the Net Oil Computer. Therefore, the fluid may not contain as much oil as output by the fluid meter. This can be problematic as a user may think the oil well is still producing a satisfactory amount of oil while the well is actually only producing water and gas. The presence of gas within the system results in equations (1) and (2) transforming into equations (3) and (4).

$$\phi_o + \phi_w + \phi_g = 1 \quad (3)$$

$$\rho_{measured} = \phi_o \rho_o + \phi_w \rho_w + \phi_g \rho_g \quad (4)$$

Where:
$\phi_g$ is the volume fraction of the gas; and
$\rho_g$ is the gas density.

As can be seen, equations (3) and (4) result in two equations, but three unknowns (the three volume fractions), which do not have a unique solution.

Another area where vibrating fluid meters are used is in the food and beverage industry. For example, in the dairy industry, users may want to know the density of the milk being delivered for various processing and quality reasons. However, often, the flowing milk includes entrained air bubbles. Therefore, for a given density provided by the vibrating fluid meter, a user cannot be sure of the density of the milk as the measured density is affected by the lower density of the air. Additionally, the volume fractions of the milk and air are unknown.

Although the problems outlined above have involved mainly liquids with entrained gas, it should be appreciated that similar problems exist with multicomponent fluids containing one or more compressible liquids mixed with one or more incompressible liquids. By "compressible" it is meant that the density of the component changes by a threshold amount within the operating conditions experienced within the system of interest. These multicomponent fluids may comprise liquids with entrained gas, two or more liquids (with at least one comprising a compressible liquid), or a gas with entrained liquid droplets.

There remains a need in the art for a vibratory fluid meter that can accurately measure flow characteristics of a multicomponent fluid with one or more incompressible fluids and one or more compressible fluids.

SUMMARY OF THE INVENTION

A method is provided according to an embodiment. The method comprises a step of measuring a first density, $\rho_1$, of a multicomponent fluid comprising one or more incompressible components and one or more compressible components at a first density state. According to an embodiment, the method further comprises a step of adjusting the multicomponent fluid from the first density state to a second density state. According to an embodiment, the method further comprises steps of measuring a second density, $\rho_2$, of the multicomponent fluid at the second density state and determining one or more fluid characteristics of at least one of the compressible components or the incompressible components.

A fluid measurement system is provided according to an embodiment. The fluid measurement system comprises a pipeline configured to receive a multicomponent fluid comprising one or more incompressible components and one or more compressible components. According to an embodiment, the fluid measurement system further comprises a first fluid meter including a first sensor assembly in fluid communication with the pipeline and a meter electronics configured to measure at least a first density, $\rho_1$, of the multicomponent fluid. According to an embodiment, the fluid measurement system further comprises a density adjustor in fluid communication with the pipeline and the first sensor assembly, configured to adjust a density of the multicomponent fluid from a first density state to at least a second density state by adjusting a pressure and/or a temperature of the multicomponent fluid. A processing system is provided that is configured to generate one or more fluid characteristics of at least one of the incompressible components or the compressible components based on the first density, $\rho_1$, of the multicomponent fluid at the first density state and a second density, $\rho_2$, of the multicomponent fluid at the second density state.

ASPECTS

According to an aspect, a method comprises steps of:
measuring a first density, $\rho_1$, of a multicomponent fluid comprising one or more incompressible components and one or more compressible components at a first density state;
adjusting the multicomponent fluid from the first density state to a second density state;
measuring a second density, $\rho_2$, of the multicomponent fluid at the second density state; and
determining one or more fluid characteristics of at least one of the compressible components or the incompressible components.

Preferably, the step of determining comprises determining a combined density of the one or more incompressible components.

Preferably, the step of measuring the first density, $\rho_1$, comprises using a first Coriolis flow meter.

Preferably, the step of measuring the second density, $\rho_2$, comprises using a second Coriolis flow meter.

Preferably, the method further comprises a step of waiting a threshold time after measuring the first density, $\rho_1$, before measuring the second density, $\rho_2$.

Preferably, the first density state comprises a first pressure, $P_1$, and a first temperature, $T_1$ and wherein the second density state comprises a second pressure, $P_2$, and/or a second temperature, $T_2$.

Preferably, the method further comprises steps of:
measuring a flow rate of the multicomponent fluid;
determining a volume fraction of one or more of the components of the multicomponent fluid; and
determining a flow rate of one or more of the components based on the measured flow rate and the volume fraction.

According to another aspect, a fluid measurement system comprises:
a pipeline configured to receive a multicomponent fluid comprising one or more incompressible components and one or more compressible components;
a first fluid meter including:
a first sensor assembly in fluid communication with the pipeline;
a meter electronics configured to measure at least a first density, $\rho_1$, of the multicomponent fluid; and
a density adjustor in fluid communication with the pipeline and the first sensor assembly, configured to adjust a density of the multicomponent fluid from a first density state to at least a second density state by adjusting a pressure and/or a temperature of the multicomponent fluid; and
a processing system configured to generate one or more fluid characteristics of at least one of the incompressible components or the compressible components based on the first density, $\rho_1$, of the multicomponent fluid at the first density state and a second density, $\rho_2$, of the multicomponent fluid at the second density state.

Preferably, the fluid measurement system further comprises a second fluid meter including:
a second sensor assembly in fluid communication with the pipeline and the density adjustor, wherein the density adjustor is positioned between the first sensor assembly and the second sensor assembly.

Preferably, the fluid measurement system further comprises a second meter electronics configured to measure at least the second density, $\rho_2$, of the multicomponent fluid at the second density state.

Preferably, the fluid measurement system further comprises one or more pressure sensors proximate the first sensor assembly and one or more pressure sensors proximate the second sensor assembly.

Preferably, a first pressure sensor is positioned upstream from the first sensor assembly and a second pressure sensor is positioned downstream from the first sensor assembly and wherein a third pressure sensor is positioned downstream from the density adjustor and upstream from the second sensor assembly and a fourth pressure sensor is positioned downstream from the second sensor assembly.

Preferably, the fluid measurement system further comprises one or more temperature sensors configured to measure a temperature of the multicomponent fluid at the first and second density states.

Preferably, the processing system comprises a part of the first meter electronics.

Preferably, the first fluid meter comprises a Coriolis flow meter.

DETAILED DESCRIPTION OF THE INVENTION

Figure 1:
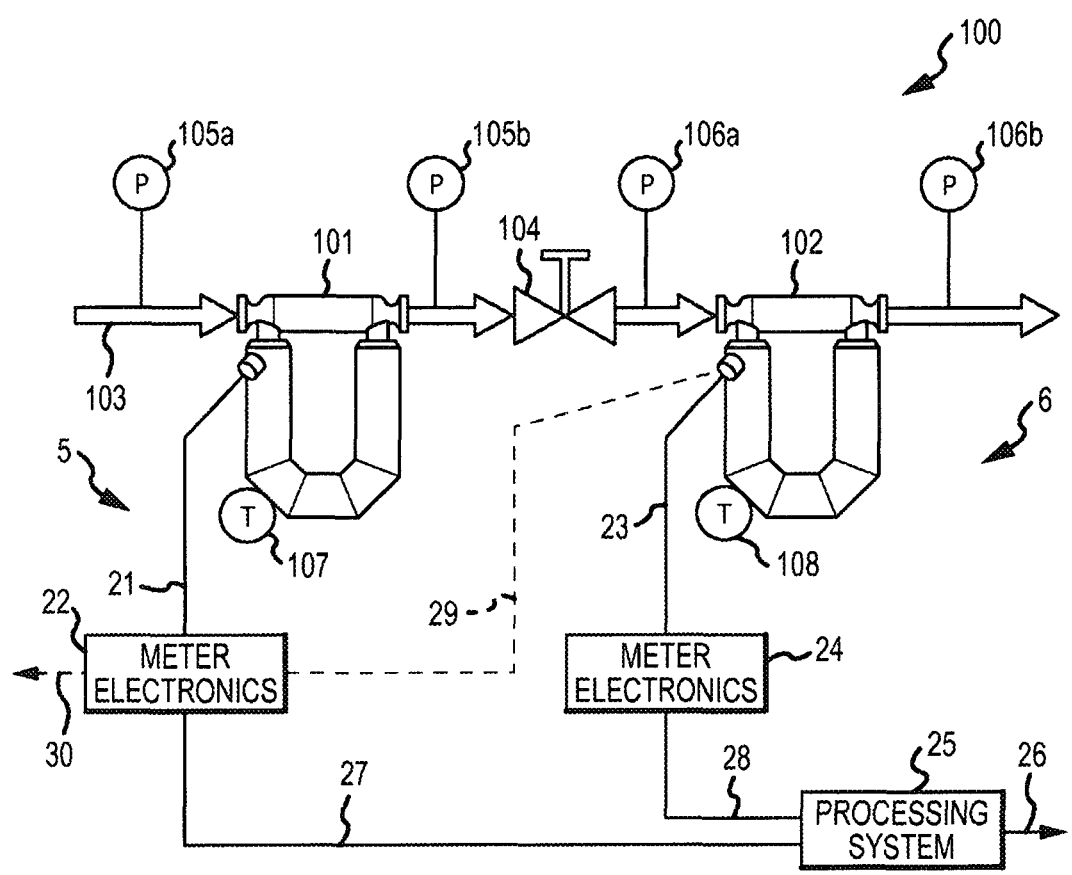
FIG. 1 shows a fluid measurement system according to an embodiment.
Figure 2:
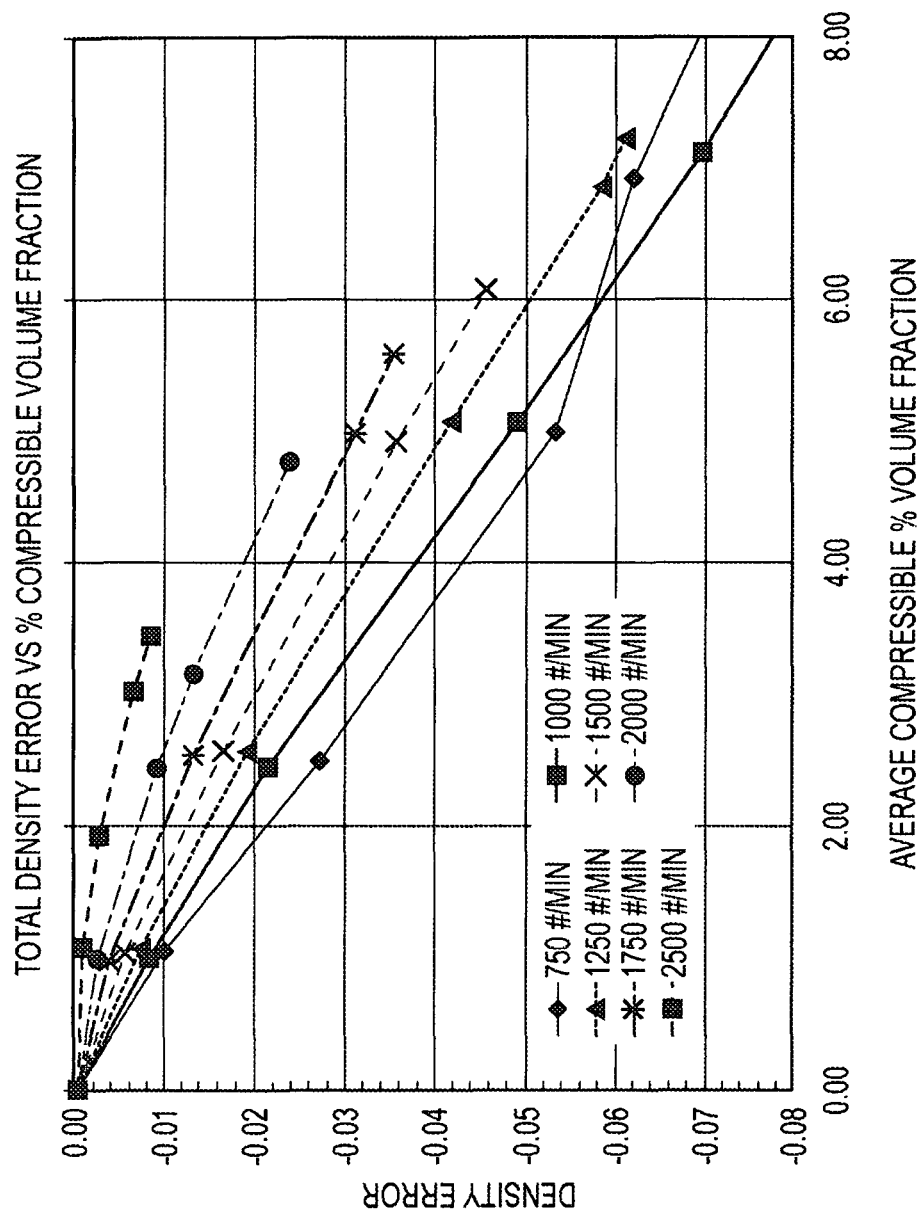
FIG. 2 shows a graph of density error from the mixture density as determined by independent gas and liquid meters versus compressible volume fraction of a fluid according to an embodiment.
Figure 3:
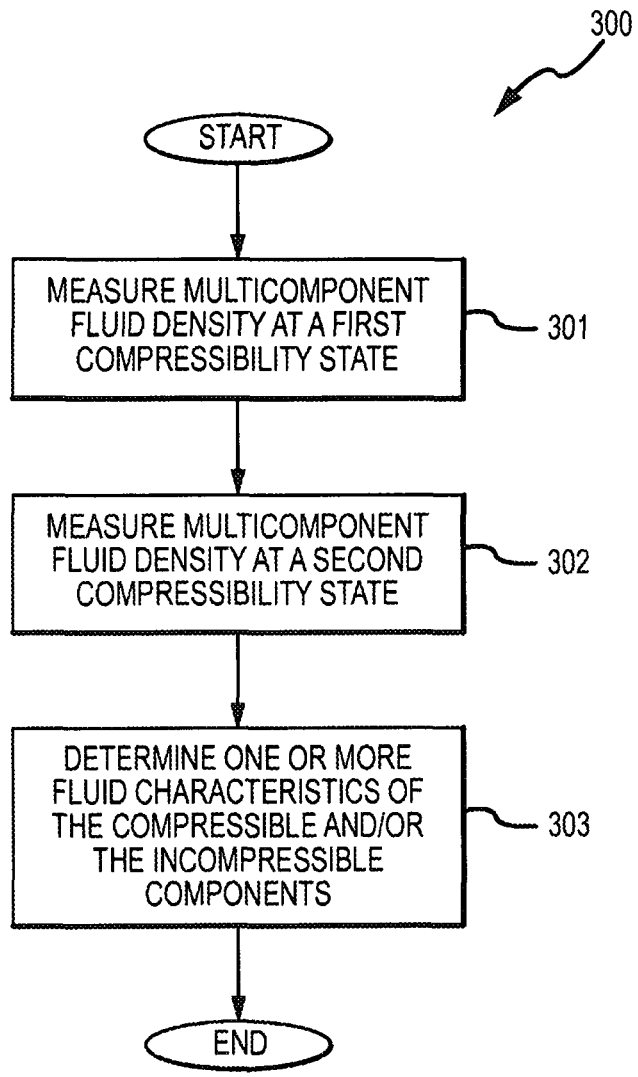
FIG. 3 shows a processing routine according to an embodiment.

FIGS. 1-3 and the following description depict specific examples to teach those skilled in the art how to make and use the best mode of embodiments of a fluid measurement system. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the fluid measurement system. As a result, the embodiments described below are not limited to the specific examples described below, but only by the claims and their equivalents.

FIG. 1 shows a fluid measurement system 100 according to an embodiment. According to an embodiment, the fluid measurement system 100 comprises a first fluid meter 5 and a second fluid meter 6. In other embodiments, a single fluid meter 5 may be provided without the second fluid meter 6. Such embodiments are most suited for situations where the fluid is not flowing as will be described in more detail below. According to an embodiment, the first fluid meter 5 comprises a sensor assembly 101 and a meter electronics 22. The sensor assembly 101 and the meter electronics 22 may be in electrical communication via one or more leads 21. According to an embodiment, the second fluid meter 6 comprises a sensor assembly 102 and a meter electronics 24. The sensor assembly 102 and the meter electronics 24 may be in electrical communication via one or more leads 23. According to the embodiment shown, the first and second fluid meters 5, 6 comprise Coriolis flow meters; however, other types of fluid meters that lack the measurement capabilities of Coriolis flow meters may be used such as for example, vibrating densitometers, etc. The particular type of fluid meter used should in no way limit the scope of the present embodiment. However, the fluid meters 5, 6 can preferably measure at least a fluid density.

According to an embodiment, the two meter electronics 22, 24 may be in electrical communication with one another. According to another embodiment, the two meter electronics 22, 24 may be in electrical communication with a common processing system 25 via leads 27, 28, respectively. The common processing system 25 can process signals received from the two meter electronics 22, 24 and output desired information to a user via lead 26. For example, the processing system 25 may receive various measurements from each of the meter electronics 22, 24 and determine one or more fluid characteristics of the multicomponent fluid based on the received measurements. Although the processing system 25 is shown as a separate component, in other embodiments, the processing system 25 may comprise a portion of one of the meter electronics 22, 24.

According to yet another embodiment, both of the sensor assemblies 101, 102 may be in electrical communication with a single meter electronics, such as the meter electronics 22 and the processing system 25 of the meter electronics 22 can perform all of the necessary signal processing and output desired information to a user via lead 30. The leads 29 and 30 are shown as dashed lines to illustrate the alternative embodiment.

According to an embodiment, the first and second sensor assemblies 101, 102 can be positioned in fluid communication with a fluid pipeline 103. The fluid pipeline 103 can receive a multicomponent fluid comprising one or more compressible components and one or more incompressible components. Once the multicomponent fluid is received in the fluid pipeline 103, at least the first fluid meter 5 can measure the multicomponent fluid density. During the measurements, the fluid may be flowing or stationary.

According to an embodiment, the first and second sensor assemblies 101, 102 are separated within the fluid pipeline 103 by a density adjustor 104. The density adjustor 104 may comprise a valve, a pump, a length of pipe, a length of pipe comprising a reduced or enlarged cross-sectional area, a heater, a chiller, etc. Those skilled in the art will readily recognize that the density adjustor 104 can comprise any type of device capable of changing the density state of the multicomponent fluid such that the density of a compressible component of the fluid flowing within the pipeline 103 changes. For example using the oil, water, gas combination above, the density adjustor 104 would be capable of changing the density of the gas while the densities of the oil and water remained the same. The density adjustor 104 is therefore provided such that the densities and thus, the volume fractions of the compressible components of the fluid are different between the first sensor assembly 101, which is at a first density state, and the second sensor assembly 102, which is at a second density state. Those skilled in the art will readily recognize that the density of compressible fluids may be changed between the two density states by adjusting the pressure and/or the temperature. For example, if the fluid is flowing through the pipeline and both the first and second fluid sensors 5, 6 are provided, the density adjustor 104 could comprise a pump that increases the pressure of the multicomponent fluid between the first and second sensor assemblies 101, 102. Alternatively, in other embodiments, the density adjustor 104 could comprise a control valve or any component through which energy in the multicomponent fluid is lost resulting in a pressure loss. The multicomponent fluid could enter the first sensor assembly 101 and comprise a first density state with a first temperature and pressure. The multicomponent fluid could then pass through a control valve or another component that results in a pressure gain or loss providing the multicomponent fluid with a second density state at second pressure and/or temperature in the second sensor assembly 102. In another embodiment, only the first sensor assembly 101 may be provided and filled with the multicomponent fluid at the first density state with a first temperature and pressure. A valve could be opened briefly to allow some of the fluid to escape and then closed again to provide the multicomponent fluid with a second density state at a second pressure and/or temperature. As can be appreciated, the density adjustor 104 does not change the density of any incompressible components of the fluid.

Also shown in FIG. 1 are upstream 105a and downstream 105b pressure sensors associated with the first sensor assembly 101 as well as upstream 106a and downstream 106b pressure sensors associated with the second sensor assembly 101. Although four pressure sensors 105a, 105b, 106a, 106b are shown in FIG. 1, it should be appreciated that less than four pressure sensors may be provided. For example, in some embodiments, only two pressure sensors may be required wherein one pressure sensor is upstream from the density adjustor 104 and another pressure sensor is downstream from the density adjustor 104. In some embodiments, providing just two pressure sensors with one upstream and one downstream can provide a close enough estimate of the pressure within the sensor assemblies 101, 102. For example, if the fluid measurement system 100 only included the pressure sensor 105a and the pressure sensor 106a, then these two pressures could be used for the calculations that follow and in some embodiments would provide close enough estimates of the actual pressures within the sensor assemblies 101, 102 to be within an acceptable tolerance. In other embodiments, only one pressure sensor may be required. This may be true in situations where only a single fluid meter is present or if the pressure drop between the two fluid meters is known or assumed based on the flow rate through the system 100.

However, providing an upstream pressure sensor 105a and a downstream pressure sensor 105b allows an average pressure of the fluid in the first sensor assembly 101 to be calculated. Likewise, the upstream pressure sensor 106a and the downstream pressure sensor 106b allows an average pressure of the fluid in the second sensor assembly 102 to be calculated.

According to an embodiment, the fluid measurement system 100 can further include first and second temperature sensors 107, 108. According to an embodiment, the first temperature sensor 107 can determine a temperature of the fluid in the first sensor assembly 101 while the second temperature sensor 108 can determine a temperature of the fluid in the second sensor assembly 102. It is generally not necessary to have a temperature sensor upstream and downstream of each fluid meter, as the temperature is unlikely to change significantly during travel through the meter. However, such additional temperature measurements could be used to improve the accuracy of the average temperature determination in each fluid meter. The first and second temperature sensors 107, 108 may comprise RTD sensors, as is generally known for fluid meters, such as Coriolis flow meters. It should be appreciated that the first and second temperature sensors 107, 108 may not directly determine a fluid temperature, but rather the fluid temperature may be determined indirectly. For example, it is known in the art to utilize one or more temperature sensors that can be coupled to the sensor assembly's flow tubes and other locations and a fluid temperature can be determined based on the one or more measured temperatures. Therefore, the first and second temperature sensors 107, 108 may comprise any of the well-known configurations used in the fluid measurement industry.

As discussed above, a problem with prior art systems is that if the fluid flowing through the measurement system comprised one or more compressible components and one or more incompressible components, a determination of the flow characteristics of the individual components was not possible. For example, with the oil, water, and gas illustration discussed above, the prior art did not provide a system for accurately determining fluid characteristics of the liquid phase (incompressible components). Rather, the prior art Coriolis flow meter was only capable of determining a total mixture density, and could not distinguish a liquid density from the gas density. Equation (2) above could not be solved because the density being measured was the total density including the gas while equation (2) requires just the liquid density. Using the fluid measurement system 100, it is possible to calculate a density of the incompressible components along with other fluid characteristics of the multicomponent fluid. If there are two incompressible components, and their individual densities are known, it would then be possible to provide an improved Net Oil Computer that essentially ignores the gas phase in calculation of parameters such as water cut (ratio of water volume fraction to the total volume) and individual liquid component flow rates, such as oil flow rate.

Although in the example of oil, water, and gas, the density of the incompressible fluid essentially comprises the combined liquid density; in other situations, the compressible component may be a compressible liquid rather than a gas. Consequently, the present embodiment is not limited to only calculating the liquid density of a liquid/gas mixture.

According to an embodiment, with the fluid measurement system 100, various fluid characteristics can be determined due to the density adjustor 104 adjusting the multicomponent fluid from a first density state to a second density state using equations of state (5-11) as follows.

$$\phi_{I1} + \phi_{C1} = 1 \tag{5}$$

$$\rho_1 = \phi_{I1}\rho_{INCOMP} + \phi_{C1}\rho_{C1} \tag{6}$$

$$\phi_{I2} + \phi_{C2} = 1 \tag{7}$$

$$\rho_2 = \phi_{I2}\rho_{INCOMP} + \phi_{C2}\rho_{C2} \tag{8}$$

$$P_1 = \rho_{C1}RT_1 \tag{9}$$

$$P_2 = \rho_{C2}RT_2 \tag{10}$$

$$\frac{P_1\varphi_{C1}}{T_1} = \frac{P_2\varphi_{C2}}{T_2} \tag{11}$$

Where the inputs that can be measured using the fluid measurement system 100 are as follows:
  $P_1$ is the fluid pressure at the first density state;
  $P_2$ is the fluid pressure at the second density state;
  $T_1$ is the temperature at the first density state;
  $T_2$ is the temperature at the second density state;
  $\rho_1$ is the density measured at the first density state; and
  $\rho_2$ is the density measured at the second density state.
With the measured inputs above, the following variables are unknown from equations (5-11):

$\phi_{I1}$ is the volume fraction of the incompressible components at the first density state;

$\phi_{I2}$ is the volume fraction of the incompressible components at the second density state;

$\phi_{C1}$ is the volume fraction of the compressible components at the first density state;

$\phi_{C2}$ is the volume fraction of the compressible components at the second density state;

$\rho_{INCOMP}$ is the combined density of the one or more incompressible components (this is assumed constant between the first and second density states);

$\rho_{C1}$ is the density of the compressible components at the first density state; and $\rho_{C2}$ is the density of the compressible components at the second density state.

As those skilled in the art will readily appreciate, this results in seven equations with seven unknowns. The seven equations can be solved as long as the density adjustor 104 changes the density of the compressible components so that two different compressible densities and void fractions are present at the first and second density states. According to the embodiment shown with the first and second sensor assemblies 101, 102, the first density state measurements can be taken by the first fluid meter 5 and the second density state measurements can be taken by the second fluid meter 6. According to one embodiment, the measurements taken by the second fluid meter 6 may be delayed from the measurements taken by the first fluid meter 5 by a threshold time. The threshold time may be based on a flow rate as determined by one of the fluid meters. The delayed processing of the signals can allow the second fluid meter 6 to measure the density of the same multicomponent fluid as measured by the first fluid meter 5. This may improve the measurements if a user or operator is concerned that the proportions of the one or more compressible components and one or more incompressible components in the fluid stream are rapidly changing. However, if the relative proportions are remaining substantially constant or changing very slowly in time, then the first and second fluid meters 5, 6 may measure the densities at substantially the same time.

However, if only one of the fluid meters is present, then both of the density state measurements will be taken by the single fluid meter at different times (before and after the density adjustor 104 adjusts the density state of the multicomponent fluid by adjusting the pressure and/or temperature).

Using the example of the oil, water, and gas again, the amount of oil and water is typically of interest, which as mentioned above, requires a known combined density of the liquid (incompressible components). Therefore, according to one embodiment, equations (5-11) can be reduced to a single equation (12) which can be solved for $\rho_{INCOMP}$.

$$0 = \left(1 - \frac{\rho_2 - \rho_{INCOMP}}{\frac{P_1}{RT_1} - \rho_{INCOMP}\frac{P_1 T_2}{T_1 P_2}}\right)\rho_{INCOMP} + \left(\frac{\rho_2 - \rho_{INCOMP}}{1 - \rho_{INCOMP}\frac{T_2 R}{P_2}}\right) - \rho_1 \quad (12)$$

Those skilled in the art will readily recognize that equation (12) is an implicit equation that requires a solver. Equation (12) can also be rewritten into an explicit solution using some substitutions as follows.

$$Z = \frac{P_2 T_1}{P_1 T_2} \quad (13)$$

$$a = z - 1 \quad (14)$$

$$b = \rho_{C2} - z\rho_2 - z\rho_{C1}\rho_1 \quad (15)$$

$$c = z\rho_{C1}\rho_2 - \rho_{C2}\rho_1 \quad (16)$$

Using equations (13-16), equation (17) provides an explicit solution for the incompressible components' density.

$$\rho_{INCOMP} = \frac{-b\left(\begin{array}{c}+\\-\end{array}\right)\sqrt{b^2 - 4ac}}{2a} \quad (17)$$

The "+" sign in equation 17 is used when the density of the compressible component in the first density state is less than the density of the compressible component in the second density state. The "−" sign in equation 17 is used when the density of the compressible component in the first density state is greater than the density of the compressible component in the second density state.

With the density of the incompressible components of the fluid calculated the water and oil volume fractions from equations (1) and (2) can be determined. Additionally, any of the unknown fluid characteristics listed above, such as the volume fraction of compressible components, can be determined. After these unknowns are determined, certain additional parameters can then be calculated, such as the water cut and flow rates for each of the individual components. For example, if at least one of the fluid meters 5, 6 comprise a flow meter, such as a Coriolis mass flow meter or a volumetric flow meter, a flow rate of the multicomponent flow can be measured. The multicomponent flow rate may comprise a mass flow rate or a volume flow rate. The multicomponent flow rate can then be multiplied by the volume fractions of the individual components to give a flow rate of the individual components.

Using two meters at two different density states, it should be appreciated that the equations listed above can solve for the densities and volume fractions of the total compressible and incompressible components. If incompressible component densities are known, as is usually the case for the Net Oil Computer, then the above algorithm can also determine up to two individual volume fractions for liquids making up the incompressible component. However, if more than three components are present in the combined stream, then more information may be required to calculate the individual fluid characteristics for each of the components.

Furthermore, those skilled in the art will readily recognize that solving the equations above requires that certain fluid conditions be maintained. For example, in order for equations (9) and (10) to be accurate, the compressible components should obey the ideal gas law. If the compressible fluid does not obey the ideal gas law, then the equations should take into account the component's compressibility factors, Z. If the compressible components are liquids, then equations (9) and (10) should be replaced by the appropriate equations of state for that fluid. These equations of state can be analytically determined, or can be lookup tables referencing experimentally determined data. Furthermore, the equations assume that the incompressible components maintain the same density between the two sensor assemblies 101, 102, i.e., the density adjustor 104 does not affect the incompressible components. This is why the densities of the incompressible fluids are not included in equations (9) and (10). Another assumption made in solving the equations is that none of the compressible components are absorbed or released from the incompressible components between the first and second density states as adjusted by the density adjustor 104. This assumption can typically be made possible if the distance between the first and second sensor assemblies 101, 102 is kept below some threshold distance, which may be determined experimentally, for example. Also, using a density adjustor that causes a pressure increase, such as a pump, rather than a pressure decrease, can help to adhere to this requirement. Further, absorption and flashing are more problematic with gases entrained in liquids than for compressible and incompressible liquid mixtures.

Those skilled in the art understand that often when a fluid comprises incompressible and compressible components, such as a liquid with entrained gas, that the compressible components cause errors in the density readings of fluid meters, such as Coriolis flow meters. The errors caused are generally due to the density of the compressible components and decoupling of the compressible fluid from the incompressible fluid. As will be shown below, the error caused by the compressible components can be ignored in solving equations (5-11) for the density of the incompressible component.

According to an embodiment, in order to prove that the error can be ignored, equation (12) can be rewritten to include the error. This is shown in equation (18).

$$0 = \left(1 - \frac{(\rho_2 - e_2) - \rho_{INCOMP}}{\frac{P_1}{RT_1} - \rho_{INCOMP}\frac{P_1T_2}{T_1P_2}}\right)\rho_{INCOMP} + \left(\frac{(\rho_2 - e_2) - \rho_{INCOMP}}{1 - \rho_{INCOMP}\frac{T_2R}{P_2}}\right) - (\rho_1 - e_1) \quad (18)$$

Where:
$e_1$ is the error when measuring $\rho_1$; and
$e_2$ is the error when measuring $\rho_2$.

Those skilled in the art will readily recognize that the errors, $e_1$ and $e_2$ can be ignored in solving equations (5-11) if the errors are both equal to zero. However, this is rarely the case. Nevertheless, if equations (12) and (18) are set equal to each other, then it can be determined what other circumstances are required for the errors to be ignored. In order to demonstrate this point most easily, the compressible fluid density is set equal to zero, which is a reasonable assumption for the case of a liquid with entrained gas at typical pressures. This proof can be done without setting the compressible fluid density to zero, but the math is more complicated; therefore, for the purposes of demonstrating the concept, the compressible fluid density is set to zero. With the compressible fluid density set to zero, equations (6) and (8) can be written as equations (19) and (20).

$$\rho_1 = \phi_{I1}\rho_{INCOMP} \quad (19)$$

$$\rho_2 = \phi_{I2}\rho_{INCOMP} \quad (20)$$

After some substitutions, which are omitted for brevity of the description, yet those skilled in the art can readily perform, the simplified forms of equations (12) and (18) can be set equal to one another as shown in equation (21) to determine the circumstances required for the errors $e_1$ and $e_2$ to be insignificant to the calculation of the density of the incompressible components.

$$\rho_{incomp} - \frac{\rho_1\rho_{incomp}}{\frac{P_1T_2}{P_2T_1}} - \rho_2 = \rho_{incomp} - \frac{\rho_1 - e_2 - \rho_{incomp}}{\frac{P_1T_2}{P_2T_1}} - \rho_2 + e_1 \quad (21)$$

Simplifying equation (21) further, it can be shown that for equations (12) and (18) to be equivalent, then equation (22) must be true.

$$e_1 = \frac{P_2T_1}{P_1T_2}e_2 \quad (22)$$

Therefore, equation (22) shows that for the decoupling and compressibility errors to be insignificant, $e_1$ and $e_2$ must be linearly related by pressure and temperature ratios. From equation (11) above, equation (22) can be rewritten in terms of volume fractions as:

$$e_1 = \frac{\varphi_{C1}}{\varphi_{C2}}e_2 \quad (23)$$

Therefore, if the compressibility and decoupling errors increase linearly with volume fraction of the incompressible component, then the solution of equations (5-11) above for the density of the incompressible component is insensitive to the presence of the compressibility and decoupling errors. Experiments have shown that there is a linear relationship between the error and the volume fraction of the compressible component, at least for Coriolis meters or densitometers relying on vibrating tube technology. This is illustrated in FIG. 2.

FIG. 2 shows a graph of the total density error from mixture density. This is determined by a density measurement of the mixture and measurements from individual gas and liquid meters prior to the two parts becoming a mixture. The various linear trend lines are taken at different flow rates. However, for each flow rate, it can be seen that as the volume fraction of the compressible component increases, the density error increases linearly. Therefore, as long as the flow rate between the first and second sensor assemblies 101, 102 remains substantially the same, the error will stay on a single trend line as shown in FIG. 2 and the density error can be ignored while solving equations (5-11). Maintaining the same flow rate through both sensor assemblies 101, 102 is typically achieved because the two sensor assemblies 101, 102 are placed in the same pipeline 103. Thus, not only does the fluid measurement system 100 provide new information and fluid characteristics of individual components not previously measurable in multicomponent fluids, it also resolves the problem of inaccurate measurements due to decoupling and compressibility errors in vibrating tube flow meters and densitometers. Even though both meters experience errors, the errors cancel out when using the algorithm described above to calculate the density of the incompressible component.

In use, the fluid measurement system 100 can be used to determine various fluid characteristics of a fluid in pipeline 103 that comprises one or more compressible components and one or more incompressible components. Routine 300 outlines one possible embodiment for determining the various fluid characteristics of at least one of the compressible or the incompressible components.

FIG. 3 shows a processing routine 300 according to an embodiment. According to an embodiment, the processing routine 300 may be performed using the first and second meter electronics 22, 24 along with the processing system 25. According to another embodiment, the processing routine 300 may be performed using one of the first or second meter electronics 22, 24. According to another embodiment, the processing routine 300 may be performed using the first and second meter electronics 22, 24 where the processing system 25 comprises a part of one of the meter electronics 22, 24.

According to an embodiment, the processing routine 300 begins in step 301 where a first density, $\rho_1$, of a multicomponent fluid is measured at a first density state. The multicomponent fluid comprises one or more compressible components and one or more incompressible components. The first density state comprises the first pressure, $P_1$ and a first temperature, $T_1$ as described above. According to an embodiment, the first density, $\rho_1$, comprises the density within the first sensor assembly 101, for example. In some embodiments, additional information about the multicomponent fluid may be determined such as a fluid flow rate, which may be determined if the first fluid meter 5 comprises a Coriolis flow meter, for example. According to an embodiment, the first density, $\rho_1$, can be determined in the first meter electronics 22, for example.

In step 302, a second density, $\rho_2$, of the multicomponent fluid is measured at a second density state. According to an embodiment, the second density state is different from the first density state. The second density state can be different due to the density adjustor 104, which can change the pressure and/or temperature of the fluid to a second pressure, $\rho_2$ and a second temperature, $T_2$. According to an embodiment, the second density, $\rho_2$, can be determined in the second meter electronics 22, for example.

According to an embodiment, the first and second density states can be determined by the one or more pressure sensors 105a, 105b, 106a, 106b and the one or more temperature sensors 107, 108, for example.

In step 303, one or more fluid characteristics of at least one of the compressible components and the incompressible components can be determined. According to an embodiment, the one or more fluid characteristics can be determined based on the first and second densities, $\rho_1$, $\rho_2$, and the first and second density states. According to an embodiment, the processing system 25 can receive the first and second densities, $\rho_1$, $\rho_2$, and determine one or more fluid characteristics, such as combined density of the one or more incompressible components, $\rho_{INCOMP}$, as discussed above. The combined incompressible component density, $\rho_{INCOMP}$, may comprise a mixture density if the multicomponent fluid includes two or more incompressible components. Alternatively, if only one incompressible component is in the multicomponent fluid, then the density, $\rho_{INCOMP}$, will simply comprise the density of the single incompressible component. As discussed above, other fluid characteristics can also be determined such as the individual volume fractions of the one or more compressible and the one or more incompressible components, a flow rate of individual components of the incompressible and compressible components of the fluid. For example, if the fluid comprises a mixture of oil, water, and gas, the individual flow rates and volume fractions of the oil, water, and gas may be determined.

The embodiments described above allow the fluid measurement system 100 to obtain fluid characteristics of at least one of an incompressible component or compressible component of a multicomponent fluid. By changing the density state of the fluid and measuring the combined fluid density at the different density states, the volume fractions and thus, fluid characteristics of the components can be determined. The fluid measurement system 100 therefore, does not have to rely upon complex and expensive separation equipment to separate compressible components from incompressible components as in the prior art. Therefore, desired information of the multicomponent fluid can be obtained in substantially real-time as the fluid is flowing through the measurement system 100.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other fluid measurement systems, and not just to the embodiments described above and shown in the accompanying figure. Accordingly, the scope of the embodiments described above should be determined from the following claims.

We claim:

1. A method, comprising steps of:
   measuring a first density, $\rho_1$, of a multicomponent fluid comprising one or more incompressible components and one or more compressible components at a first density state;
   adjusting the multicomponent fluid from the first density state to a second density state;
   measuring a second density, $\rho_2$, of the multicomponent fluid at the second density state; and
   determining one or more fluid characteristics of at least one of the compressible components or the incompressible components.

2. The method of claim 1, wherein the step of determining comprises determining a combined density of the one or more incompressible components.

3. The method of claim 1, wherein the step of measuring the first density, $\rho_1$, comprises using a first Coriolis flow meter.

4. The method of claim 1, wherein the step of measuring the second density, $\rho_2$, comprises using a second Coriolis flow meter.

5. The method of claim 1, further comprising a step of waiting a threshold time after measuring the first density, $\rho_1$, before measuring the second density, $\rho_2$.

6. The method of claim 1, wherein the first density state comprises a first pressure, $P_1$, and a first temperature, $T_1$ and wherein the second density state comprises a second pressure, $P_2$, and/or a second temperature, $T_2$.

7. The method of claim 1, further comprising steps of:
   measuring a flow rate of the multicomponent fluid;
   determining a volume fraction of one or more of the components of the multicomponent fluid; and
   determining a flow rate of one or more of the components based on the measured flow rate and the volume fraction.

8. A fluid measurement system (100), comprising:
   a pipeline (103) configured to receive a multicomponent fluid comprising one or more incompressible components and one or more compressible components;
   a first fluid meter (5) including:

a first sensor assembly (101) in fluid communication with the pipeline (103);

a meter electronics (22) configured to measure at least a first density, $\rho_1$, of the multicomponent fluid; and a density adjustor (104) in fluid communication with the pipeline (103) and the first sensor assembly (101), configured to adjust a density of the multicomponent fluid from a first density state to at least a second density state by adjusting a pressure and/or a temperature of the multicomponent fluid; and a processing system (25) configured to generate one or more fluid characteristics of at least one of the incompressible components or the compressible components based on the first density, $\rho_1$, of the multicomponent fluid at the first density state and a second density, $\rho_2$, of the multicomponent fluid at the second density state.

9. The fluid measurement system (100) of claim 8, further comprising a second fluid meter (6) including:

a second sensor assembly (102) in fluid communication with the pipeline (103) and the density adjustor (104), wherein the density adjustor (104) is positioned between the first sensor assembly (101) and the second sensor assembly (102).

10. The fluid measurement system (100) of claim 9, further comprising a second meter electronics (24) configured to measure at least the second density, $\rho_2$, of the multicomponent fluid at the second density state.

11. The fluid measurement system (100) of claim 9, further comprising one or more pressure sensors (105*a*, 105*b*) proximate the first sensor assembly (101) and one or more pressure sensors (106*a*, 106*b*) proximate the second sensor assembly (102).

12. The fluid measurement system (100) of claim 11, wherein a first pressure sensor (105*a*) is positioned upstream from the first sensor assembly (101) and a second pressure sensor (105*b*) is positioned downstream from the first sensor assembly (101) and wherein a third pressure sensor (106*a*) is positioned downstream from the density adjustor (104) and upstream from the second sensor assembly (102) and a fourth pressure sensor (106*b*) is positioned downstream from the second sensor assembly (102).

13. The fluid measurement system (100) of claim 8, further comprising one or more temperature sensors configured to measure a temperature of the multicomponent fluid at the first and second density states.

14. The fluid measurement system (100) of claim 8, wherein the processing system (25) comprises a part of the first meter electronics (22).

15. The fluid measurement system (100) of claim 8, wherein the first fluid meter (5) comprises a Coriolis flow meter.

* * * * *